US010153502B2

(12) United States Patent
Pijpers (10) Patent No.: US 10,153,502 B2
(45) Date of Patent: Dec. 11, 2018

(54) ELECTROCHEMICAL SYSTEMS INCORPORATING IN SITU SPECTROSCOPIC DETERMINATION OF STATE OF CHARGE AND METHODS DIRECTED TO THE SAME

(71) Applicant: Lockheed Martin Energy, LLC, Bethesda, MD (US)

(72) Inventor: Joseph Johannes Henricus Pijpers, Cambridge, MA (US)

(73) Assignee: Lockheed Martin Energy, LLC, Bethesda, MD (US)

(*) Notice: Subject to any disclaimer, the term of this patent is extended or adjusted under 35 U.S.C. 154(b) by 335 days.

(21) Appl. No.: 14/963,147

(22) Filed: Dec. 8, 2015

(65) Prior Publication Data

US 2016/0164125 A1    Jun. 9, 2016

Related U.S. Application Data

(60) Provisional application No. 62/088,856, filed on Dec. 8, 2014.

(51) Int. Cl.
*H01M 8/18* (2006.01)
*G01R 31/36* (2006.01)
(Continued)

(52) U.S. Cl.
CPC ...... *H01M 8/04477* (2013.01); *G01N 21/552* (2013.01); *H01M 8/04604* (2013.01);
(Continued)

(58) Field of Classification Search
CPC .................................................. G01N 21/552
See application file for complete search history.

(56) References Cited

U.S. PATENT DOCUMENTS 5,942,102 A    8/1999  Hodges et al.
6,413,410 B1   7/2002  Hodges et al.
(Continued)

FOREIGN PATENT DOCUMENTS

CA    2236848 A1    5/1997
CA    2823963 A1    7/2012
(Continued)

OTHER PUBLICATIONS

Extended European Search Report from European Patent Application No. 14862634.4, dated May 11, 2017.
(Continued)

*Primary Examiner* — Jonathan Crepeau
(74) *Attorney, Agent, or Firm* — Baker & Hostetler LLP (57) ABSTRACT

State of charge determination within electrochemical systems, such as flow batteries, can often be difficult to measure, particularly in an in situ manner. Methods for assaying the condition of an electrochemical system can include: interacting electromagnetic radiation with a first electrolyte solution at a location within the electrochemical system, the electromagnetic radiation being delivered through an optical material configured to exhibit attenuated total reflectance at an interface between the optical material and the first electrolyte solution; receiving at a detector electromagnetic radiation that has interacted with the first electrolyte solution via one or more attenuated total reflectances within the optical material; and measuring an absorbance of at least one of an oxidized form or a reduced form of a first coordination compound within the first electrolyte solution via the electromagnetic radiation that is received at the detector.

20 Claims, 3 Drawing Sheets

(51) Int. Cl.
*G01N 21/552* (2014.01)
*H01M 8/0444* (2016.01)
*H01M 8/04537* (2016.01)
*G01N 21/85* (2006.01)

(52) U.S. Cl.
CPC ........ *H01M 8/188* (2013.01); *G01N 21/8507* (2013.01); *G01R 31/3606* (2013.01); *Y02E 60/528* (2013.01)

(56) References Cited

U.S. PATENT DOCUMENTS

| | | | |
|---|---|---|---|
| 8,587,255 | B2 | 11/2013 | Parakulam et al. |
| 8,980,484 | B2 | 3/2015 | Chang et al. |
| 2003/0170906 | A1 | 9/2003 | Swain et al. |
| 2005/0158614 | A1 | 7/2005 | Hennessy |
| 2006/0049064 | A1* | 3/2006 | Horvath ............... C07D 491/10 205/687 |
| 2008/0060196 | A1 | 3/2008 | Wang et al. |
| 2008/0193828 | A1 | 8/2008 | Sahu |
| 2008/0204708 | A1 | 8/2008 | Shaw |
| 2009/0026094 | A1 | 1/2009 | Deng et al. |
| 2010/0047671 | A1 | 2/2010 | Chiang et al. |
| 2010/0084288 | A1 | 4/2010 | Hodges et al. |
| 2011/0081563 | A1 | 4/2011 | Christensen et al. |
| 2011/0086247 | A1 | 4/2011 | Keshavarz et al. |
| 2011/0223450 | A1 | 9/2011 | Horne et al. |
| 2012/0263986 | A1 | 10/2012 | Fulop et al. |
| 2013/0011702 | A1 | 1/2013 | Horne et al. |
| 2013/0029185 | A1 | 1/2013 | Ridley et al. |
| 2013/0084482 | A1 | 4/2013 | Chang et al. |
| 2013/0084506 | A1 | 4/2013 | Chang et al. |
| 2013/0095362 | A1 | 4/2013 | Keshavarz et al. |
| 2013/0157162 | A1 | 6/2013 | Dong et al. |
| 2013/0224538 | A1 | 8/2013 | Jansen et al. |
| 2013/0269566 | A1 | 10/2013 | Van Polen |
| 2014/0030631 | A1 | 1/2014 | Esswein et al. |
| 2014/0238875 | A1 | 8/2014 | Bekki et al. |
| 2014/0299014 | A1 | 10/2014 | Van Polen |
| 2016/0111740 | A1 | 4/2016 | Spaziante et al. |
| 2016/0254562 | A1 | 9/2016 | Morris-Cohen et al. |
| 2016/0293979 | A1 | 10/2016 | King et al. |
| 2016/0293991 | A1 | 10/2016 | Goeltz et al. |
| 2016/0372777 | A1 | 12/2016 | Buckley et al. |

FOREIGN PATENT DOCUMENTS

| | | |
|---|---|---|
| CN | 1204400 A | 1/1999 |
| EP | 1998163 A1 | 12/2008 |
| EP | 2648258 A1 | 10/2013 |
| JP | 2004-336734 A | 11/2004 |
| JP | 2006-351346 A | 12/2006 |
| WO | WO-90/03666 A1 | 4/1990 |
| WO | WO-2008/148148 A1 | 12/2008 |
| WO | WO-2010/118175 A2 | 10/2010 |
| WO | WO-2012/094674 A2 | 7/2012 |

OTHER PUBLICATIONS

Corcuera et al., "State-of-charge monitoring and electrolyte rebalancing methods for the vanadium redox flow battery," European Chemical Bulletin, 2012, pp. 511-519, vol. 1.

Mohamed et al., "Estimating the State-of-Charge of all-Vanadium Redox Flow Battery using a Divided, Open-circuit Potentiometric Cell," Elektronika IR Elektrotechnika, 2013, pp. 39-41, vol. 19.

Pop et al., "State-of-the-art of battery state-of-charge determination," Measurement Science and Technology, 2005, pp. R93-R110, vol. 16.

Skyllas-Kazacos et al., "State of charge monitoring methods for vanadium redox flow battery control," J Power Science, 2011, pp. 8822-8827, vol. 196.

Extended European Search Report from European Application No. 14858186.1, dated Apr. 26, 2017.

Soloveichik, "Flow Batteries: Current Status and Trends," 2015, Chem. Rev., 115 (20), pp. 11533-11558.

International Search Report and Written Opinion from PCT/US16/65160, dated Feb. 17, 2017.

Extended European Search Report from European Patent Application No. 15868031.4, dated Jun. 7, 2018, 8 pages.

* cited by examiner

ELECTROCHEMICAL SYSTEMS INCORPORATING IN SITU SPECTROSCOPIC DETERMINATION OF STATE OF CHARGE AND METHODS DIRECTED TO THE SAME

CROSS-REFERENCE TO RELATED APPLICATIONS

The present application claims the benefit of priority under 35 U.S.C. § 119 from U.S. Provisional Patent Application 62/088,856, filed on Dec. 8, 2014 and incorporated herein by reference in its entirety.

STATEMENT REGARDING FEDERALLY SPONSORED RESEARCH OR DEVELOPMENT

Not applicable.

FIELD

The present disclosure generally relates to energy storage and, more specifically, to flow batteries and associated electrochemical systems for energy storage.

BACKGROUND

Electrochemical energy storage systems, such as batteries, supercapacitors and the like, have been widely implemented for large-scale energy storage applications. Various battery designs, including flow batteries, have been adopted for this purpose. Compared to other types of electrochemical energy storage systems, flow batteries can be advantageous, particularly for large-scale applications, due to their ability to decouple the parameters of power density and energy density from one another through the disposition of their active materials. Alternately, flow batteries can be considered to decouple power output and energy storage from one another. As used herein, the terms "active material," "electroactive material," "redox-active material" or related variants thereof will refer to materials that undergo a change in oxidation state during operation of an electrochemical cell.

Flow batteries generally include negative and positive active materials in corresponding electrolyte solutions, which are flowed separately across opposing sides of a membrane or separator in an electrochemical cell. The battery is charged or discharged through electrochemical reactions of the active materials that occur inside the cell. The electrochemical reactions result in oxidation or reduction of the active materials during charging or discharging.

State of charge is an important operating parameter for flow batteries and other electrochemical systems utilizing electrolyte solutions. The term "state of charge (SOC)" is a well understood electrochemical energy storage term that will refer herein to the relative amounts of reduced species and oxidized species at an electrode within a half-cell of an electrochemical system. For the negative electrolyte solution, the state of charge is defined by the concentration of the reduced species divided by the total concentration of active materials in the negative electrolyte solution. For the positive electrolyte solution, the state of charge is defined by the concentration of the oxidized species divided by the total concentration of active materials in the positive electrolyte solution. For example, when equal amounts of oxidized and reduced species are present, an electrochemical system has a state of charge of 50%. The state of charge values for the individual half-cells in an electrochemical system are not necessarily equal to one another, and the state of charge for the full cell depends on the state of charge values for individual half-cells. Among other reasons, parasitic reactions (e.g., $H_2$ evolution, $H_2O$ oxidation, carbon corrosion, and the like) can occur at one or both electrodes of an electrochemical system to result in an unbalanced state of charge between the two half-cells.

It can frequently be desirable to monitor state of charge in an electrochemical system in order to provide for more reliable and efficient operation. An unbalanced state of charge can produce several detrimental effects during operation of an electrochemical system. For example, an unbalanced state of charge between the electrolyte solutions of a flow battery can lead to mass transport limitations at one of the electrodes, thereby lowering the round-trip operating efficiency. An accurate measurement of state of charge can allow one to determine the degree of cell rebalancing that is needed to restore the flow battery to more optimal operating conditions.

Despite the desirability for knowing state of charge in an electrochemical system, ready techniques for accurately measuring state of charge are presently lacking, particularly in situ measurement techniques. In situ measurements can be desirable in order to preclude changes in the proportion of oxidized and reduced forms of the active materials that can sometimes occur during offline laboratory analyses (e.g., exposure to air and other like reactive conditions that are not reflective of the electrochemical system's operating environment). One conventional technique for in situ determination of state of charge involves use of an oxidation-reduction probe (ORP). However, the probe output is prone to drift over time, and the accuracy of the state of charge measurement can suffer as a result.

In view of the foregoing, electrochemical systems incorporating ready determination of state of charge and methods associated therewith would be highly desirable in the art. The present disclosure satisfies the foregoing needs and provides related advantages as well.

SUMMARY

In some embodiments, the present disclosure provides methods for determining the condition of electrochemical systems. The methods can include: providing an electrochemical system containing a first electrolyte solution in contact with a first electrode, where the first electrolyte solution contains a first coordination compound having an oxidized form and a reduced form; interacting electromagnetic radiation with the first electrolyte solution at a location within the electrochemical system such that the electromagnetic radiation is delivered through an optical material configured to exhibit attenuated total reflectance at an interface between the optical material and the first electrolyte solution; receiving at a detector electromagnetic radiation that has interacted with the first electrolyte solution via one or more attenuated total reflections within the optical material; and measuring an absorbance of at least one of the oxidized form or the reduced form of the first coordination compound with the electromagnetic radiation that is received at the detector. The optical material has a higher index of refraction than does the first electrolyte solution.

In other various embodiments, the present disclosure provides electrochemical systems in which the operating condition can be determined in situ. The electrochemical systems can include: a first electrolyte solution in contact with a first electrode, where the first electrolyte solution includes a first coordination compound having an oxidized form and a reduced form; a source of electromagnetic radiation; an optical material establishing optical communication between the source of electromagnetic radiation and the first electrolyte solution; and a detector configured to receive electromagnetic radiation from the optical material that has interacted with the first electrolyte solution via one or more attenuated total reflections at the interface between the optical material and the first electrolyte solution. The optical material is configured to exhibit attenuated total reflectance at the interface between the optical material and the first electrolyte solution, where the optical material has a higher index of refraction than does the first electrolyte solution.

The foregoing has outlined rather broadly the features of the present disclosure in order that the detailed description that follows can be better understood. Additional features and advantages of the disclosure will be described hereinafter. These and other advantages and features will become more apparent from the following description.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

The present disclosure is directed, in part, to electrochemical systems, such as flow batteries, in which state of charge and other cell parameters can be measured in situ. The present disclosure is also directed, in part, to methods for measuring state of charge and other cell parameters in situ within an electrochemical system, such as a flow battery.

The present disclosure may be understood more readily by reference to the following description taken in connection with the accompanying figures and examples, all of which form a part of this disclosure. It is to be understood that this disclosure is not limited to the specific products, methods, conditions or parameters described and/or shown herein. Further, the terminology used herein is for purposes of describing particular embodiments by way of example only and is not intended to be limiting unless otherwise specified. Similarly, it is to be recognized that where the disclosure describes a cell, flow battery, or other electrochemical energy storage system, it is appreciated that methods for operating the cell, flow battery, or other electrochemical energy storage system are also implicitly described.

It is also to be appreciated that certain features of the present disclosure may be described herein in the context of separate embodiments for clarity purposes, but may also be provided in combination with one another in a single embodiment. That is, unless obviously incompatible or specifically excluded, each individual embodiment is deemed to be combinable with any other embodiment(s) and the combination is considered to represent another distinct embodiment. Conversely, various features of the present disclosure that are described in the context of a single embodiment for brevity's sake may also be provided separately or in any sub-combination. Finally, while a particular embodiment may be described as part of a series of steps or part of a more general structure, each step or sub-structure may also be considered an independent embodiment in itself.

Unless stated otherwise, it is to be understood that each individual element in a list and every combination of individual elements in that list is to be interpreted as a distinct embodiment. For example, a list of embodiments presented as "A, B, or C" is to be interpreted as including the embodiments "A," "B," "C," "A or B," "A or C," "B or C," or "A, B, or C."

In the present disclosure the singular forms of the articles "a," "an," and "the" also include the corresponding plural references, and reference to a particular numerical value includes at least that particular value, unless the context clearly indicates otherwise. Thus, for example, reference to "a material" is a reference to at least one of such materials and equivalents thereof.

In general, use of the term "about" indicates approximations that can vary depending on the desired properties sought to be obtained by the disclosed subject matter and is to be interpreted in a context-dependent manner based on functionality. Accordingly, one having ordinary skill in the art will be able to interpret a degree of variance on a case-by-case basis. In some instances, the number of significant figures used when expressing a particular value may be a representative technique for determining the variance permitted by the term "about." In other cases, the gradations in a series of values may be used to determine the range of variance permitted by the term "about." Further, all ranges in the present disclosure are inclusive and combinable, and references to values stated in ranges include every value within that range.

As discussed above, it is presently difficult to determine state of charge and other operating parameters in various electrochemical systems, such as flow batteries, particularly in an in situ manner. Oxidation-reduction probes can sometimes be used for in situ determination of state of charge, but they are often prone to drift over time.

From an operational standpoint, it can be highly desirable to have freely soluble active materials in the electrolyte solutions of a flow battery in order to avoid deposition of circulating particulates. As used herein, the term "solution" will refer to the condition of being at least partially dissolved, ideally fully dissolved. Since the storage capacity (energy density) of an electrochemical system often depends on the amounts of active materials that are present in the electrolyte solutions, high-solubility active materials can be desirable in order to produce high-concentration solutions.

UV-VIS spectroscopy is another technique that can sometimes be used to determine state of charge based on the differences in electromagnetic radiation absorption between the oxidized and reduced forms of the active material in an electrolyte solution. UV-VIS measurements are commonly performed in a transmission configuration, in which a monochromatic or broadband beam of electromagnetic radiation is passed through a sample and the intensity of the transmitted light is measured at a detector. Under transmission conditions, the Beer-Lambert law (Equation 1) can be used to relate the concentration and absorbance values to one another $$A = \varepsilon CL \qquad \text{(Equation 1)}$$

in which A is the measured absorbance, $\varepsilon$ is the molar absorptivity constant of the substance being analyzed, C is the substance's concentration, and L is the path length through which the electromagnetic radiation is transmitted. For substances having relatively low molar absorptivity constants (e.g., less than about 50 $M^{-1}cm^{-1}$), path lengths on the order of about 1 cm or greater can be used to produce absolute absorbance values in a range of about 0.05 to about 2 in the typical concentration ranges present in electrolyte solutions (e.g., about 0.5 M to about 4 M). For substances having lower molar absorptivity constants, longer path lengths can be used to retain the absolute absorbance in this range. Absolute absorbance values within this range can be highly desirable to avoid decreased signal-to-noise at the low end and detector saturation at the high end of this range.

Although low molar absorptivity constants can be addressed by increasing the transmission path length, high molar absorptivity constants and/or high concentrations can be much more difficult to address, particularly for in situ analyses. Specifically, the transmission path length can only be decreased so far before significant operational difficulties set in. At transmission path lengths below about 1 mm in length, and particularly below about 0.1 mm in length, a narrow flow field results, and it can be easily obstructed by even small amounts of circulating particulates. Thus, for active materials that strongly absorb electromagnetic radiation, conventional transmission absorbance spectroscopy is wholly impractical for in situ determination of state of charge. In many cases, the practical working limit for common electrolyte solution concentrations can be reached for molar absorptivity constants of about 100 $M^{-1}cm^{-1}$ or greater. Many active materials of interest, including various metal-ligand coordination compounds, can display molar absorptivity constants above this threshold, sometimes significantly above in the case of ligands such as porphyrins.

The present inventor identified that attenuated total reflectance (ATR) spectroscopy can be used to determine state of charge in an electrochemical system, such as a flow battery, particularly in situations where conventional transmission spectroscopy is unsuitable from a practical standpoint. In particular, ATR spectroscopy can be used effectively in situations where highly absorbing electrolyte solutions would otherwise require excessively small path lengths for conventional transmission spectroscopy. Thus, provided that the absorbance of at least one of the oxidized or reduced forms of the active material in a half-cell can be quantified with a chosen type of electromagnetic radiation, the absorbance can then be correlated to the state of charge as described hereinafter. For example, by knowing the concentration of one of the oxidized or reduced forms, the concentration of the other form can be inferred based upon the total concentration of the active material. Ideally, the absorbances of both the oxidized and reduced forms of the active material are determined directly by ATR spectroscopy to provide a more reliable measurement. If desired, the state of charge of each half-cell can be determined independently by ATR spectroscopic techniques to provide the operating condition of the full cell. For example, the difference between the state of charge values for the two half-cells can provide a metric for initiating a rebalancing or reconditioning of the flow battery. A detailed description of ATR spectroscopy as it is applied to electrochemical systems, including flow batteries, follows hereinbelow. Advantageously, mechanisms for conducting ATR spectroscopic measurements can be readily incorporated within various electrochemical systems in order to conduct various operational analyses, including determination of state of charge.

The electrochemical systems and methods of the present disclosure can be further advantageous by virtue of their operability in situ within the electrochemical system. Thus, the systems and methods of the present disclosure mitigate the need for sampling and handing of potentially reactive, corrosive, and/or toxic materials by laboratory personnel. Because sampling can occur in situ within the electrochemical system at any suitable location, the condition of the electrolyte solution under its true operating conditions can be more accurately assayed than would otherwise be possible upon sampling and handing the electrolyte solution during laboratory analyses. Further, more rapid feedback regarding the condition of the electrolyte solution can be determined than is possible by offline analysis techniques. Suitable locations for the conducting the ATR spectroscopic measurements within an electrochemical system are addressed in further detail hereinbelow. Finally, probes for performing ATR spectroscopy and detection systems are relative non-prone toward drift, thereby making them advantageous with respect to ORP measurements that are conventionally used.

Electrochemical systems incorporating a mechanism for performing ATR spectroscopy on an electrolyte solution in at least one of the half-cells of the electrochemical system are described herein. By performing ATR spectroscopy on the electrolyte solution, various operating parameters of the electrochemical system can be determined, including the state of charge of the electrolyte solution. In illustrative embodiments, the electrochemical system can be a flow battery.

In various embodiments, the electrochemical systems of the present disclosure can include a first electrolyte solution in contact with a first electrode, a source of electromagnetic radiation, an optical material establishing optical communication between the source of electromagnetic radiation and the first electrolyte solution, and a detector configured to receive electromagnetic radiation from the optical material that has interacted with the first electrolyte solution via one or more attenuated total reflectances at the interface between the optical material and the first electrolyte solution. The optical material has a higher index of refraction than does the first electrolyte solution, and is configured to exhibit attenuated total reflectance at the interface between the optical material and the first electrolyte solution. The first electrolyte solution contains a first coordination compound having an oxidized form and a reduced form. That is, the first coordination compound serves as an active material in the first electrolyte solution.

As used herein, the term "coordination compound" will refer to a metal ion that is complexed by one or more ligands, particularly by at least one chelating ligand. As used herein, the term "chelating ligand" will refer to a ligand that binds a metal ion simultaneously at two or more locations. In some embodiments, the ligand(s) can be an organic compound containing C, H, N and/or O atoms. In some embodiments, the coordination compound can include at least one ligand that is not water, hydroxide, or halide. Other illustrative ligands that can be present in a coordination compound of the present disclosure are discussed in further detail below. The chemical nature of the ligands can alter the redox potential of the ligated metal ion, thereby allowing some degree of tailoring to be realized in the operating characteristics of an electrolyte solution containing the coordination compound. Coordination compounds can also have an altered solubility profile compared to non-ligated metal ions (e.g. solubility at different pH values and/or solubility in organic solvents).

In general, the electrolyte solution(s) within any type of electrochemical system can be analyzed according to the disclosure here. Illustrative electrochemical systems can include, for example, conventional batteries, flow batteries, supercapacitors, fuel cells, and the like. A particular configuration for an illustrative flow battery is described in more detail hereinafter (see FIG. 2). Although a flow battery has been described as a particular electrochemical system in which ATR spectroscopy can be used for conducting electrolyte solution analyses, it is to be recognized that electrolyte solutions in other types of electrochemical systems can be analyzed similarly.

It is to be further recognized that certain portions of the description herein are only expressly described as being directed to mechanisms and methods for analyzing the electrolyte solution for one half-cell of an electrochemical system (i.e., a first electrolyte solution containing a first coordination compound). However, it is to be recognized that the electrolyte solution for the other half-cell of the electrochemical system (i.e., a second electrolyte solution containing a second coordination compound) can be analyzed independently from the other electrolyte solution, if desired. That is, the first electrolyte solution and the second electrolyte solution of the electrochemical system can both be analyzed, if desired, where at least one of the first and second electrolyte solutions is analyzed by the ATR spectroscopy techniques described herein. In some embodiments, both the first and second electrolyte solutions can be analyzed by the ATR spectroscopy techniques described herein.

Figure 1:
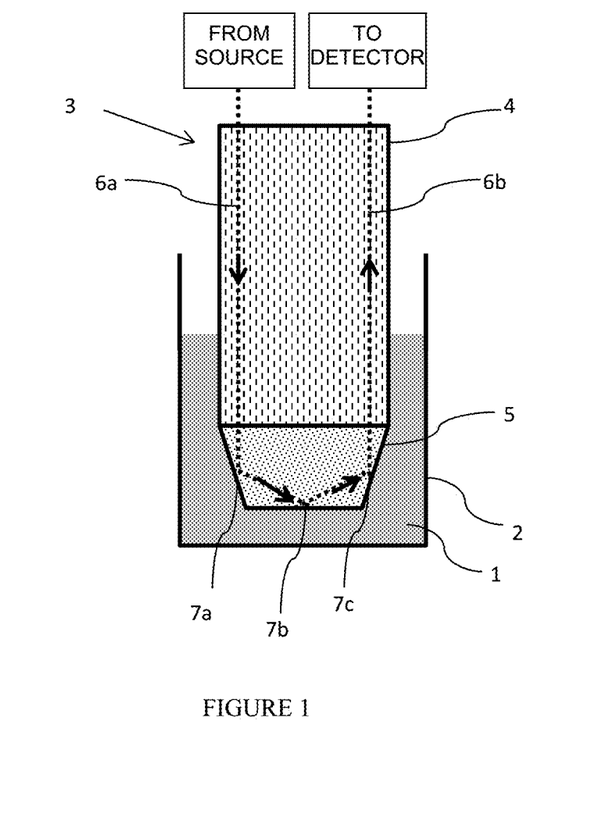
FIG. 1 shows an illustrative schematic of an electrolyte solution containing a probe incorporating an optical material configured for attenuated total reflectance.

FIG. 1 shows an illustrative schematic of an electrolyte solution containing a probe incorporating an optical material configured for attenuated total reflectance. As shown in FIG. 1, electrolyte solution 1 is contained in housing 2. Although housing 2 is shown as being an open container in FIG. 1, it can also be closed. Probe 3 contains probe body 4 and optical material 5. Probe body 4 and optical material 5 are in optical communication with a source and a detector, such that electromagnetic radiation 6a can be interacted with electrolyte solution 1, and altered electromagnetic radiation 6b can be returned to the detector. Optical material 5 is a substance that can exhibit attenuated total reflectance at its interface with electrolyte solution 1. Considerations for choosing optical material 5 are discussed in more detail hereinbelow.

As shown in FIG. 1, three points of internal reflection (7a, 7b and 7c) occur within optical material 5 before electromagnetic radiation 6b is returned to the detector for analysis. At each internal reflection, an evanescent wave penetrates slightly into electrolyte solution 1 and optically interacts with the reduced and/or oxidized form(s) of the active material before being reflected to the succeeding reflection point. This results in a very short effective path length for the optical interaction (e.g., about 0.05 microns to about 2 microns), much shorter than would be possible in a transmission configuration. With each succeeding reflection, the effective path length increases. Hence, the number of internal reflections can be varied to produce an effective path length that is sufficient to provide good detection signal-to-noise but without saturating the detector. For example, the number of internal reflections can be selected based upon the molar absorptivity constant of the active material in electrolyte solution 2 and its concentration. Optical materials 5 are available in geometries that can provide a wide range of internal reflections, but 1 to about 6 internal reflections are common. Hence, the three reflections depicted in FIG. 1 should not be considered limiting.

As shown above, an optical material capable of attenuated total reflectance (i.e., internal reflection) is in contact with the first electrolyte solution in order to determine the condition of the first electrolyte solution, such as the state of charge of the first electrolyte solution. In order for internal reflection to occur, the optical material has a higher index of refraction than does the first electrolyte solution, provided that other conditions for attenuated total reflection to occur are met. Otherwise, electromagnetic radiation passing through the optical material escapes into the first electrolyte solution, and internal reflection in the form of an evanescent wave does not occur. In more specific embodiments, the optical material capable of internal reflection can have a refractive index of greater than about 1.3. More typically, the optical material can have a refractive index ranging between about 1.3 and about 6, and even more typically a refractive index ranging between about 1.5 and about 2.5. Suitable optical materials (n=refractive index) for use in the various embodiments of the present disclosure can include, for example, sapphire (n=1.77), germanium (n=4.05), silicon (n=3.48), fused silica (n=1.46), quartz (n=1.54), cubic zirconia (n=2.11), zinc selenide, (n≥2.4), diamond (n=2.41) and any combination thereof. These optical materials and other substances having high refractive indices can be particularly suitable for facilitating attenuated total reflectance measurements of aqueous solutions. Except for germanium and silicon, the foregoing optical materials can be particularly useful in the ultraviolet and visible regions of the electromagnetic spectrum. In general, the optical material provides optical transparency for the incoming and outgoing electromagnetic radiation. In various embodiments, the optical material that is capable of attenuated total reflectance can be a crystalline material. The crystalline material can be single crystalline or polycrystalline in various embodiments.

In various embodiments, the optical material can be in a prismatic form that can facilitate at least one internal reflection at an interface with the first electrolyte solution before the electromagnetic radiation is returned to the detector. In more particular embodiments, the optical material can be configured to provide between 1 and about 6 attenuated total reflectances at the interface with the first electrolyte solution. In some embodiments, the optical material can be in a cone-shaped geometry, which can provide 2 attenuated total reflections. Optical materials configured for providing a number of attenuated total reflections within this range are available from several commercial sources.

The angle of incidence of the incident electromagnetic radiation (i.e., electromagnetic radiation received from the source) can also dictate whether attenuated total reflectance takes place within the optical material. The angle of incidence below which attenuated total reflectance takes place is referred to as the "critical angle." One having ordinary skill in the art will be able to determine a range of angles of incidence over which attenuated total reflectance can occur for a particular optical material geometry configured to provide a given number of internal reflections.

As indicated above, electromagnetic radiation internally reflecting within the optical material can establish an evanescent wave that penetrates slightly into the first electrolyte solution and interacts with the electrolyte solution at one or more points. In some embodiments, the evanescent wave can exhibit a depth of penetration into the first electrolyte solution in a range between about 0.05 microns and about 2 microns. The depth of penetration represents an effective path length at each point of reflection. The actual depth of penetration will be dependent upon a number of factors including, for example, the angle of incidence, the refractive index of the optical material, the refractive index of the first electrolyte solution, and the wavelength of the incident electromagnetic radiation.

In various embodiments, the first electrolyte solution can be an aqueous solution. As used herein, the terms "aqueous solution" or "aqueous electrolyte" will refer to any solution in which water is the predominant component, including solutions containing a water-miscible organic solvent as a minority component. Illustrative water-miscible organic solvents that can be present in an aqueous electrolyte include, for example, alcohols and glycols, optionally in the presence of one or more surfactants. In more specific embodiments, an aqueous solution can contain at least about 98% water by weight. In other embodiments, an aqueous solution can contain at least about 40% water by weight, or at least about 45% water by weight, or at least about 50% water by weight, or at least about 55% water by weight, or at least about 60% water by weight, or at least about 65% water by weight, or at least about 70% water by weight, or at least about 75% water by weight, or at least about 80% water by weight, or at least about 85% water by weight, or at least about 90% water by weight, or at least about 95% water by weight. In some embodiments, the aqueous solution can be free of water-miscible organic solvents and consist of water alone as a solvent.

In other various embodiments, the first electrolyte solution can be non-aqueous and include an organic solvent. In general, any organic solvent that is electrochemically stable under the electrochemical system's operating conditions can be used for solubilizing an active material.

In various embodiments, the first coordination compound present within the first electrolyte solution can include at least one transition metal ion and at least one ligand. Illustrative ligands that can be present in the coordination compound include, for example, substituted or unsubstituted catecholates, ascorbate, citrate, glycolate, a polyol, gluconate, hydroxyalkanoate, acetate, formate, benzoate, malate, maleate, phthalate, sarcosinate, salicylate, oxalate, urea, polyamine, aminophenolate, acetylacetonate, and lactate. Where chemically feasible, it is to be recognized that these ligands can be optionally substituted with at least one group selected from among $C_{1-6}$ alkoxy, $C_{1-6}$ alkyl, $C_{1-6}$ alkenyl, $C_{1-6}$ alkynyl, 5- or 6-membered aryl or heteroaryl groups, a boronic acid or a derivative thereof, a carboxylic acid or a derivative thereof, cyano, halide, hydroxyl, nitro, sulfonate, a sulfonic acid or a derivative thereof, a phosphonate, a phosphonic acid or a derivative thereof, or a glycol, such as polyethylene glycol. Alkanoate includes any of the alpha, beta, and gamma forms of these ligands. Polyamines include, but are not limited to, ethylenediamine, ethylenediamine tetraacetic acid (EDTA), and diethylenetriamine pentaacetic acid (DTPA).

In some or other various embodiments, monodentate ligands that can be present in the first coordination compound of the first electrolyte solution include, for example, halides, cyanide, carbonyl or carbon monoxide, nitride, oxo, hydroxo, water, sulfide, thiols, pyridine, pyrazine, and the like. Other examples of bidentate ligands that can be present in the first coordination compound of the first electrolyte solution include, for example, bipyridine, bipyrazine, ethylenediamine, diols (including ethylene glycol), and the like. Other examples of tridentate ligands that can optionally be present in the first coordination compound of the first electrolyte solution include, for example, terpyridine, diethylenetriamine, triazacyclononane, tris(hydroxymethyl)aminomethane, and the like. Other acceptable ligands can include quinones, hydroquinones, viologens, acridinium, polycyclic aromatic hydrocarbons and combinations thereof.

In more specific embodiments, the first coordination compound that is present in the first electrolyte solution can have a formula of $$A_xM(L_1)(L_2)(L_3),$$

in which M is a transition metal, A is $NH_4^+$ or tetraalkylammonium ($C_1$-$C_4$ alkyl), $Na^+$, $K^+$ or any combination thereof, x is an integer ranging between 1 and 6, and $L_1$, $L_2$ and $L_3$ are ligands that can be independently selected from the lists above. In more specific embodiments, at least one of $L_1$, $L_2$ and $L_3$ can be a chelating ligand. In still more specific embodiments, at least one of $L_1$, $L_2$ and $L_3$ can be a catecholate or substituted catecholate ligand.

Due to their variable oxidation states, transition metals can constitute the positive and/or negative active materials in various embodiments of a flow battery. Cycling between the accessible oxidation states can result in the conversion of chemical energy into electrical energy. Lanthanide elements can be used similarly in this regard. In general, any transition metal or lanthanide metal can be present in the first coordination compound of the first electrolyte solution. In some embodiments, the transition metal can be selected from among Al, Cr, Ti and Fe. For purposes of the present disclosure, Al is to be considered a transition metal. In more specific embodiments, the transition metal can be Ti. Other suitable transition and main group metals that can be present in the first coordination compound of the first electrolyte solution include, for example, Ca, Ce, Co, Cu, Mg, Mn, Mo, Ni, Pd, Pt, Ru, Sr, Sn, V, Zn, Zr, and any combination thereof. In various embodiments, the first coordination compound can include a transition metal in a non-zero oxidation state when the transition metal is in both its oxidized and reduced forms. Cr, Fe, Mn, Ti and V can be particularly desirable in this regard.

In addition to a solvent and a coordination compound as an active material, the first electrolyte solution can also include one or more mobile ions. In some embodiments, mobile ions can include proton, hydronium, or hydroxide. In other various embodiments, mobile ions other than proton, hydronium, or hydroxide can be present, either alone or in combination with proton, hydronium or hydroxide. Such alternative mobile ions can include, for example, alkali metal or alkaline earth metal cations (e.g., $Li^+$, $Na^+$, $K^+$, $Mg^{2+}$, $Ca^{2+}$ and $Sr^{2+}$) and halides (e.g., $F^-$, $Cl^-$, or $Br^-$). Other mobile ions can include, for example, ammonium and tetraalkylammonium ions, chalcogenides, phosphate, hydrogen phosphate, phosphonate, nitrate, sulfate, nitrite, sulfite, perchlorate, tetrafluoroborate, hexafluorophosphate, and any combination thereof. In some embodiments, less than about 50% of the mobile ions can constitute protons, hydronium, or hydroxide. In other various embodiments, less than about 40%, less than about 30%, less than about 20%, less than about 10%, less than about 5%, or less than about 2% of the mobile ions can constitute protons, hydronium, or hydroxide.

In further embodiments, the first electrolyte solution can also include one or more additional additives such as, but not limited to, a buffer, a supporting electrolyte, a viscosity modifier, a wetting agent, or any combination thereof. Illustrative buffers can include, but are not limited to, salts of phosphates, borates, carbonates, silicates, tris(hydroxymethyl)aminomethane (tris), 4-(2-hydroxyethyl)-1-piperazineethanesulfonic acid (hepes), piperazine-N,N'-bis(ethanesulfonic acid) (pipes), or any combination thereof. Other examples of suitable buffers and the other additional additives will be familiar to one having ordinary skill in the art In various embodiments, a concentration of the first coordination compound in the first electrolyte solution can range between about 0.1 M and about 3 M. This concentration range represents the sum of the individual concentrations of the oxidized and reduced forms of the first coordination compound. In more particular embodiments, the concentration of the first coordination compound can range between about 0.5 M and about 3 M, or between 1 M and about 3 M, or between about 1.5 M and about 3 M, or between 1 M and about 2.5 M. In other more specific embodiments, a concentration of the first coordination compound can range between about 1 M and about 1.8 M in an aqueous electrolyte solution.

The first electrolyte solution can exhibit any pH in a range of about 1 to about 14. In more specific embodiments, the first electrolyte solution can contain a first coordination compound and have a pH ranging between about 1 and about 13, or between about 2 and about 12, or between about 4 and about 10, or between about 6 and about 8, or between about 1 and about 7, or between about 7 and about 13, or between about 8 and about 13, or between about 9 and about 14, or between about 10 and about 13, or between about 9 and about 12. Suitable pH ranges for the first electrolyte solution can be chosen based upon the stability and/or solubility of the first coordination compound and/or its ligands at a given pH, and such consideration can be determined by one having ordinary skill in the art.

As indicated above, ATR spectroscopy can be particularly suitable for analyzing electrolyte solutions which contain coordination compounds that exhibit high molar absorptivity constants. The high molar absorptivity constants can be exhibited by the oxidized form of the coordination compounds, the reduced form of the coordination compounds, or both. In more specific embodiments, the first coordination compound in the first electrolyte solution can have a molar absorptivity constant of at least about 100 $M^{-1}cm^{-1}$. In more specific embodiments, the first coordination compound in the first electrolyte solution can have a molar absorptivity constant ranging between about 100 $M^{-1}cm^{-1}$ and about 1,000,000 $M^{-1}cm^{-1}$. In further embodiments, the first coordination compound in the first electrolyte solution can have a molar absorptivity constant having a lower value of about 100 $M^{-1}cm^{-1}$, 500 $M^{-1}cm^{-1}$, 1000 $M^{-1}cm^{-1}$, 2500 $M^{-1}cm^{-1}$, 5000 $M^{-1}cm^{-1}$, 7500 $M^{-1}cm^{-1}$, 10,000 $M^{-1}cm^{-1}$, 25,000 $M^{-1}cm^{-1}$, 50,000 $M^{-1}cm^{-1}$, 75,000 $M^{-1}cm^{-1}$, 100,000 $M^{-1}cm^{-1}$, 250,000 $M^{-1}cm^{-1}$, or 500,000 $M^{-1}cm^{-1}$ and ranging to an upper value of about 1,000,000 $M^{-1}cm^{-1}$, 500,000 $M^{-1}cm^{-1}$, 250,000 $M^{-1}cm^{-1}$, 100,000 $M^{-1}cm^{-1}$, 50,000 $M^{-1}cm^{-1}$, 25,000 $M^{-1}cm^{-1}$, or 10,000 $M^{-1}cm^{-1}$. The molar absorptivity constant can further reside within any subrange between these low end and high end values, even though not specifically disclosed herein.

As further indicated above, both the concentration of the coordination compound and its molar absorptivity constant can dictate the suitability for its analysis by ATR spectroscopy. In some embodiments, a product (i.e., an arithmetic product) of concentration and molar absorptivity constant can be at least about 100 $cm^{-1}$. In more specific embodiments, the product of concentration and molar absorptivity constant can range between about 100 $cm^{-1}$ and about 1,000,000 $cm^{-1}$. In still further embodiments, the product of concentration and molar absorptivity constant for the coordination compound in the first electrolyte solution can have a lower value of about 100 $cm^{-1}$, 500 $cm^{-1}$, 1000 $cm^{-1}$, 2500 $cm^{-1}$, 5000 $cm^{-1}$, 7500 $cm^{-1}$, or 10,000 $cm^{-1}$ and ranging to an upper value of about 1,000,000 $cm^{-1}$, 100,000 $cm^{-1}$, 50,000 $cm^{-1}$, 10,000 $cm^{-1}$, 5000 $cm^{-1}$, 1000 $cm^{-1}$, or 500 $cm^{-1}$. The product of concentration and molar absorptivity constant can further reside within any subrange between these low end and high end values, even though not specifically disclosed herein.

In some embodiments, the electromagnetic radiation that is interacted with the first electrolyte solution can include one or more wavelengths ranging between about 180 nm and about 800 nm. That is, the electromagnetic radiation that is interacted with the first electrolyte solution can reside within the ultraviolet and/or visible region of the electromagnetic spectrum. The first coordination compound within the first electrolyte solution can absorb one or more wavelengths of electromagnetic radiation within this range or another range suitable for analysis. In more specific embodiments, the electromagnetic radiation that is interacted with the first electrolyte solution can include one or more wavelengths ranging between about 180 nm and about 300 nm, or between about 300 nm and about 400 nm, or between about 400 nm and about 500 nm, or between about 500 nm and about 600 nm, or between about 600 nm and about 700 nm, or between about 700 nm and about 800 nm. Any subrange or combination of these ranges is also considered to be expressly disclosed herein. That is, the absorbances at one or one more wavelengths can be analyzed individually or as a portion of a spectrum. Moreover, the one or more wavelengths can be monitored, measured, and/or analyzed either continuously or periodically, including through pulsing of the source of electromagnetic radiation.

Accordingly, various embodiments of methods for determining the condition of an electrolyte solution can include assaying the electrolyte solution by ATR spectroscopy, and determining the concentration and/or the absorbance of at least one of an oxidized form or a reduced form of a coordination compound that is an active material in the electrolyte solution. The absorbance(s) and/or concentration(s) of the oxidized and/or reduced forms of the coordination compound can then be correlated to the state of charge of a half-cell containing the electrolyte solution, such as that of a flow battery, as discussed hereinafter. The condition of the electrolyte solution within the other half-cell of the electrochemical system can be analyzed in a similar manner, if desired. Analyses of the electrolyte solutions within the two half-cells can occur independently of one another.

In more particular embodiments, methods for determining the condition of an electrolyte solution can include: providing an electrochemical system containing a first electrolyte solution in contact with a first electrode, interacting electromagnetic radiation with the first electrolyte solution at a location within the electrochemical system in which the electromagnetic radiation is delivered through an optical material configured to exhibit attenuated total reflectance at an interface between the optical material and the first electrolyte solution, receiving at a detector electromagnetic radiation that has interacted with the first electrolyte solution via one or more attenuated total reflections within the optical material, and measuring an absorbance of at least one of an oxidized form or a reduced form of a first coordination compound in the first electrolyte solution with the electromagnetic radiation that is received at the detector. In order to promote attenuated total reflectance, the optical material has a higher index of refraction than does the first electrolyte solution. Further, an angle of incidence of the electromagnetic radiation upon the optical material can promote attenuated total reflectance.

In further embodiments, methods of the present disclosure can further include determining a concentration of at least one of the oxidized form or the reduced form of the first coordination compound based upon the absorbance measured at the detector. In some or other embodiments, methods of the present disclosure can further include determining a state of charge of the first electrolyte solution in the electrochemical system.

As indicated above, the electrochemical system can be a flow battery in some embodiments. Exemplary description of a flow battery is provided hereinbelow, along with exemplary locations in a flow battery where analysis of the first electrolyte solution can take place. The locations where analyses can take place generally can be extended to other types of applicable electrochemical systems.

In various embodiments, the concentration of either the oxidized form or the reduced form of the first coordination compound in the first electrolyte solution can be determined in accordance with the present disclosure. Assuming that the total concentration of the oxidized form plus the reduced form of the first coordination compound remains constant, one can infer the concentration of one form based upon the concentration of the other. That is, if the initial concentration is known for the oxidized (or reduced) form of the first coordination compound in a fully charged first electrolyte solution, the concentration of either the oxidized or reduced form can be determine by subtracting the measured concentration from the initial concentration. In other various embodiments, the concentrations of both the oxidized form and the reduced form of the first coordination compound can be determined directly by the techniques of the present disclosure in the course of determining a state of charge of the first electrolyte solution.

When measuring the absorbance(s) of the oxidized form and/or the reduced form of the first coordination compound in the first electrolyte solution, the absorbance can be measured at a single wavelength, or at more than one wavelength. A spectrum may or may not be obtained when analysis takes place over multiple wavelengths.

In more particular embodiments, at least one of the wavelengths at which the oxidized form and/or the reduced form of the first coordination compound is analyzed can correspond to a local maximum in the corresponding absorbance spectrum. In more particular embodiments, at least one of the wavelengths can be a local maximum for one of the oxidized form or the reduced form of the first coordination compound, and a location of zero or near-zero absorbance (i.e., a local minimum) for the opposite form of the first coordination compound. As one of ordinary skill in the art will recognize, measurement of the absorbance at a local maximum can be desirable so that the rate of change of absorbance is at its lowest, thereby minimalizing errors resulting from spectral drift. Ideally, the opposite form of the first coordination compound displays substantially zero or minimal absorbance at the wavelengths being analyzed for the opposite form of the first coordination compound. Thus, in such embodiments, the absorbance at the local maximum substantially represents that attributable to the form of the first coordination compound being analyzed.

In still further embodiments, a first absorbance can be measured at a first wavelength for one of the oxidized form or the reduced form of the first coordination compound, and a second absorbance can be measured at a second wavelength for the opposite form of the first coordination compound. Ideally, the form of the first coordination compound measured at the first wavelength displays an absorption maximum at that wavelength, and the opposing form of the first coordination compound displays substantially zero or minimal absorbance at that wavelength. Correspondingly, the opposing form of the first coordination compound measured at the second wavelength can display an absorption maximum at that wavelength, and the form of the first coordination compound measured at the first wavelength can display substantially zero or minimal absorbance at the second wavelength. One having ordinary skill in the art can determine suitable wavelengths for analysis of each form of the first coordination compound and an amount of absorbance for the opposing form that can be tolerated at each wavelength.

In still more specific embodiments, an absorbance for the oxidized form of the first coordination compound can be measured at a first local maximum, and an absorbance for the reduced form of the first coordination compound can be measured at a second local maximum. The local maxima for the oxidized and reduced forms of the first coordination compound can differ from one another. In some embodiments, an absorbance for the oxidized form of the first coordination compound is measured at a local maximum for the oxidized form, and an absorbance for the reduced form of the first coordination compound is measured at a local maximum for the reduced form.

In some embodiments, the absorbance can be measured at least at an isosbestic point exhibited by the oxidized form and the reduced form of the first coordination compound. As one having ordinary skill in the art will recognize, isosbestic points are one or more wavelengths in an absorbance plot where the absorbance is invariant as the concentrations of two absorbing materials change (e.g., as a result of a chemical reaction). That is, as the absorbance of one material decreases to form a second material, the absorbance of the second material increases by a corresponding amount to maintain a constant absorbance. This implies that the two molar absorptivity constants are relatively similar to one another. Accordingly, in the case of a coordination compound having both oxidized and reduced forms, the absorbance at the isosbestic point represents the total concentration of both coordination compound forms. Hence, the overall concentration of the first coordination compound in the first electrolyte solution can be monitored by comparing the fixed absorbance at the isosbestic point to that measured initially at that wavelength. A decrease in the isosbestic point absorbance can indicate that active material has been lost from the first electrolyte solution, possibly indicating the need to take corrective action.

Accordingly, in some embodiments, methods of the present disclosure can include measuring an absorbance for an oxidized form or a reduced form of the first coordination compound at a first wavelength, and also measuring absorbance at an isosbestic point at a second wavelength. Hence, the absorbance of the oxidized form or the reduced form measured at the first wavelength can be applied to determine state of charge, and the absorbance at the second wavelength can be correlated to total concentration. These values can be measured simultaneously or sequentially.

Once the concentrations of the oxidized and reduced forms of the first coordination compound have been determined, the state of charge of the first electrolyte solution can then be determined by calculating the ratio of the oxidized form of the first coordination compound to the total concentration (Equation 2)

$$SOC = 100\% \times C_{ox}/(C_{red} + C_{ox}) \qquad \text{Equation 2}$$

where $C_{ox}$ is the concentration of the oxidized form of the first coordination compound and $C_{red}$ is the concentration of the reduced form of the first coordination compound. Equation 2 assumes that the oxidized form of the first coordination compound is the active material in a state of full charge. However, if the reduced form of the first coordination compound is instead the active material when charged, $C_{red}$ will replace $C_{ox}$ in the numerator of Equation 2. Accordingly, the SOC can range between 0% (fully discharged) and 100% (fully charged). As discussed above, the concentrations of the oxidized and reduced forms of the first coordination compound can be determined by measuring the absorbances at appropriate wavelengths. The measured absorbances can then be converted into absorbance values, if needed, by applying the Beer-Lambert law, a lookup table, or a calibration plot of absorbance versus concentration.

In some embodiments, the state of charge can be determined at a single wavelength, provided that either the oxidized form or the reduced form of the first coordination compound is transparent (i.e., non-absorbing) at the chosen wavelength. Thus, at the chosen wavelength, the measured absorbance is due solely to only one of the forms of the first coordination compound. In single-wavelength measurements where the oxidized form of the first coordination compound is absorbing and the reduced form of the first coordination compound is non-absorbing, the state of charge can be calculated using Equation 3

$$SOC = 100\% \times (1 - A_{meas}/A_{ox}) \quad \text{(Equation 3)}$$

in which $A_{meas}$ is the measured absorbance at the chosen wavelength, and $A_{ox}$ is the measured absorbance when only the oxidized form of the first coordination compound is present in the first electrolyte solution. $A_{ox}$ can be a previously measured value, such as when the first electrolyte solution is first formulated or the electrochemical system is fully charged or discharged. Again, Equation 3 assumes the reduced species is the active form. For the opposite electrolyte solution (i.e., the positive electrolyte solution) in which the oxidized species is the active form, the state of charge can be determined by the expression $SOC = 100\% \times (A_{meas}/A_{ox})$. In the case where the reduced form of the first coordination compound is absorbing and the oxidized form is transparent, the state of charge can be determined by the expression $SOC = 100\% \times (A_{meas}/A_{red})$, where $A_{red}$ is the absorbance of the reduced form. For the opposite electrolyte solution, the expression for determining state of charge would instead be $SOC = 100\% \times (1 - A_{meas}/A_{red})$. In further embodiments, the determination of state of charge can be conducted at two different wavelengths where either the oxidized form or the reduced form of the first coordination compound is non-absorbing in order to provide an independent assessment of the state of charge. In still further embodiments, the determination of state of charge can be made a first wavelength where the oxidized form of the first coordination compound is absorbing and the reduced form of the first coordination compound is non-absorbing, and at a second wavelength where the reduced form of the first coordination compound is absorbing and the oxidized form of the first coordination compound is non-absorbing.

In still further embodiments, the slope of the absorption spectrum can be measured at a given wavelength and correlated to state of charge. As the state of charge changes, the slope of the absorption spectrum can change in a corresponding manner. The slope of the absorption spectrum can be determined, for example, by fitting a tangent line to the absorption spectrum and measuring the slope of the tangent line. The measured slope can then be correlated (e.g., via a lookup table or a computer database) to the actual state of charge.

As indicated above, when measuring the condition of a full cell, a first electrolyte solution and a second electrolyte solution can be independently assayed using the techniques of the present disclosure. If one determines that either of the electrolyte solutions is not in a desired condition, the condition of either of the electrolyte solutions can be adjusted. For example, if the first electrolyte solution and the second electrolyte solution are out of balance, one or both of the electrolyte solutions can be adjusted to restore balance. It is to be recognized, however, that one or both of the electrolyte solutions can be adjusted without conducting an independent assay of the other. For example, a pre-defined set of conditions can be set for one or both of the electrolyte solutions, and should the first electrolyte solution enter an out-of-range condition as determined by the techniques of the present disclosure, an operator or automation software can take corrective action to rectify the situation.

Accordingly, methods of the present disclosure can include adjusting at least the first electrolyte solution based upon its state of charge. In further embodiments, adjusting the first electrolyte solution can include at least one of reconditioning or rebalancing the first electrolyte solution, diluting the first electrolyte solution, adding a further amount of the first coordination compound to the first electrolyte solution, increasing a current passing through the electrolyte solution, decreasing a current passing through the electrolyte solution, or any combination thereof. Suitable techniques and equipment for reconditioning or rebalancing an electrolyte solution will be familiar to one having ordinary skill in the art. For example, reconditioning or rebalancing the electrolyte solution can involve a chemical or electrochemical oxidation or reduction of the first coordination compound that is present in the first electrolyte solution.

Further techniques for adjusting the first electrolyte solution can involve altering a flow rate of the first electrolyte solution in the particular case of a flow battery, increasing or decreasing the current density in a galvanostatic operation or the voltage in a potentiostatic operation, and/or increasing or decreasing the power input or output.

As discussed above, the electrochemical systems described hereinabove can constitute a flow battery in some embodiments. Discussion of exemplary flow batteries follows hereinafter, including locations within the flow batteries at which an electrolyte solution can be assayed by the techniques disclosed herein to determine state of charge.

In various embodiments, flow batteries can include: a first chamber containing a negative electrode contacting a first electrolyte solution; a second chamber containing a positive electrode contacting a second electrolyte solution, and a separator disposed between the first and second electrolyte solutions. The electrolyte chambers provide separate reservoirs within the cell, through which the first and/or second electrolyte solutions circulate so as to contact the respective electrodes and the separator. Each chamber and its associated electrode and electrolyte solution define a corresponding half-cell. The separator provides several functions which include, for example, (1) serving as a barrier to mixing of the first and second electrolyte solutions and their active materials, (2) electrically insulating to reduce or prevent short circuits between the positive and negative electrodes, and (3) to facilitate ion transport between the positive and negative electrolyte chambers, thereby balancing electron transport during charge and discharge cycles. The negative and positive electrodes provide a surface where electrochemical reactions can take place during charge and discharge cycles. During a charge or discharge cycle, electrolyte solutions can be transported from separate storage tanks through the corresponding electrolyte chambers. In a charging cycle, electrical power can be applied to the cell such that the active material contained in the second electrolyte solution undergoes a one or more electron oxidation and the active material in the first electrolyte solution undergoes a one or more electron reduction. Similarly, in a discharge cycle the active material in the second electrolyte solution is reduced and the active material in the first electrolyte is oxidized to generate electrical power.

In more specific embodiments, illustrative flow batteries can include: (a) a first aqueous electrolyte solution containing a first coordination compound; (b) a second aqueous electrolyte solution containing a second coordination compound; (c) a separator positioned between said first and second aqueous electrolyte solutions; and (d) a mobile ion in the first and second aqueous electrolyte solutions. As described in more detail below, the separator can be an ionomer membrane, and it can have a thickness of less than 100 microns and have an associated net charge that is the same sign as that of the first and second coordination compounds. In some various embodiments, one of the first and second coordination compounds can be a redox couple of ferricyanide [$Fe(CN)_6^{3-}$] and ferrocyanide [$Fe(CN)_6^{4-}$]. In more specific embodiments, the ferricyanide/ferrocyanide redox couple can be used as a first coordination compound in a first electrolyte solution and the second coordination compound in a second electrolyte solution can be a coordination compound containing at least one catecholate ligand.

Figure 2:
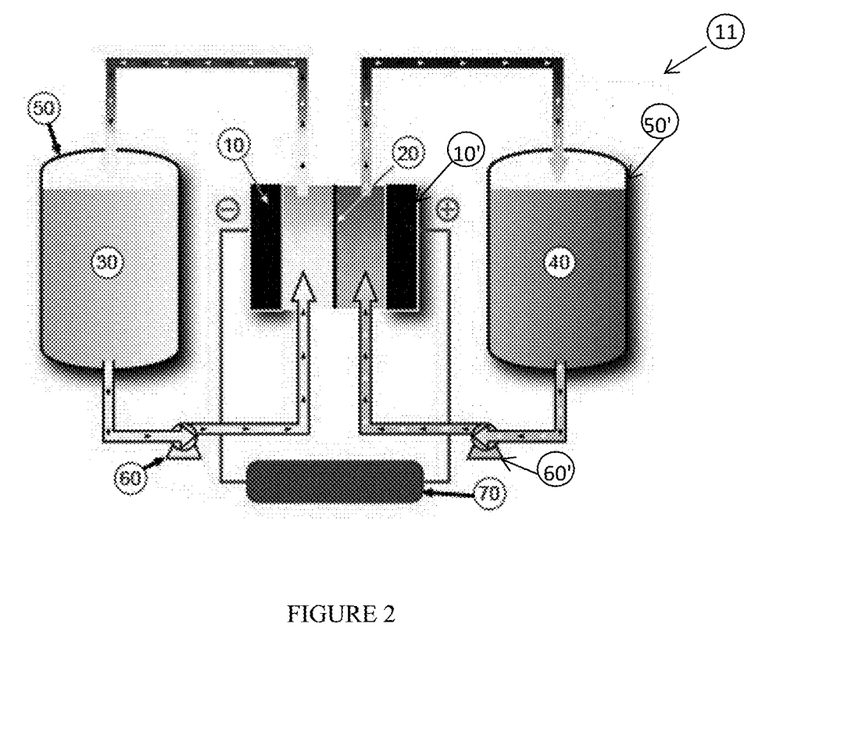
FIG. 2 depicts a schematic of an illustrative flow battery.

FIG. 2 depicts a schematic of an illustrative flow battery. Unlike typical battery technologies (e.g., Li-ion, Ni-metal hydride, lead-acid, and the like), where active materials and other components are housed in a single assembly, flow batteries transport (e.g., via pumping) redox active energy storage materials from storage tanks through an electrochemical stack. This design feature decouples the electrical energy storage system power from the energy storage capacity, thereby allowing for considerable design flexibility and cost optimization.

As shown in FIG. 2, flow battery system 11 includes an electrochemical cell that features separator 20 (e.g., a membrane) that separates the two electrodes 10 and 10' of the electrochemical cell. Electrodes 10 and 10' are formed from a suitably conductive material, such as a metal, carbon, graphite, and the like. Tank 50 contains first active material 30 in a first electrolyte solution, which material is capable of being cycled between an oxidized and reduced state. For example, first active material 30 can be a coordination compound.

Pump 60 affects transport of first active material 30 from tank 50 to the electrochemical cell. The flow battery also suitably includes second tank 50' that contains second active material 40. Second active material 40 can be the same material as active material 30, or it can be different. For example, second active material 40 can be ferricyanide/ferrocyanide, as described above. Second pump 60' can affect transport of second active material 40 to the electrochemical cell. Pumps can also be used to affect transport of the active materials from the electrochemical cell back to tanks 50 and 50' (not shown in FIG. 2). Other methods of affecting fluid transport, such as siphons, for example, can also suitably transport first and second active materials 30 and 40 into and out of the electrochemical cell. Also shown in FIG. 2 is power source or load 70, which completes the circuit of the electrochemical cell and allows a user to collect or store electricity during its operation.

It should be understood that FIG. 2 depicts a specific, non-limiting embodiment of a flow battery. Accordingly, flow batteries consistent with the spirit of the present disclosure can differ in various aspects relative to the configuration of FIG. 2. As one example, a flow battery system can include one or more active materials that are solids, gases, and/or gases dissolved in liquids. Active materials can be stored in a tank, in a vessel open to the atmosphere, or simply vented to the atmosphere.

Before further discussing the various components of a flow battery further, it should be noted that the mechanism for conducting ATR spectroscopy can be incorporated at any point within flow battery system 11. In some embodiments, the electromagnetic radiation can be interacted with the first electrolyte solution in proximity to the first electrode. For purposes of the present disclosure, the phrase "in proximity to the first electrode" will refer to any location within the chambers (not labelled in FIG. 2) that are defined between separator 20 and electrodes 10 and 10'. In other various embodiments, the electromagnetic radiation can be interacted with the first electrolyte solution at any point external to the cell defining the flow battery. For purposes of the present disclosure, the phrase "external to the cell" will refer to any point that is not within the chambers defined between electrodes 10 and 10' and separator 20. In illustrative embodiments, the electromagnetic radiation can be interacted with the first electrolyte solution within tanks 50 or 50', or at any point within the lines conveying the first electrolyte solution into and out of the cell.

The optical material delivering the electromagnetic radiation to the first electrolyte solution and providing one or more internal reflections therein can be in any suitable form when incorporated within a flow battery or other electrochemical system. In some embodiments, the optical material can constitute at least a portion of a probe that is incorporated at a given location within the electrochemical system. In some or other embodiments, the optical material can be physically mounted in the electrochemical system, such as in the form of a flow-through cell, for example. In other embodiments, the optical material can be incorporated in the electrochemical system temporarily or "on-demand," such as through insertion of a portable probe at a suitable location.

In some embodiments, electromagnetic radiation can be conveyed to and/or from the optical material by suitable transmission media such as fiber optic materials. That is, the electromagnetic radiation source, the fiber optic material, the optical material configured for attenuated total reflectance, and the detector can be disposed in series with one another. In some embodiments, a first optical fiber channel can convey the electromagnetic radiation to the optical material, and a second optical fiber channel can convey the electromagnetic radiation that has experienced attenuated total reflectance back to the detector.

Suitable detectors are not believed to be particularly limited. In some embodiments, a suitable detector can be a photodiode array detector.

It should be further understood that the first electrolyte solution can be flowing or static when being interacted with electromagnetic radiation according to the present disclosure. Similarly, the first electrolyte solution can be in a condition of undergoing charge or discharge during interaction with the electromagnetic radiation, or it can be in a static charging or discharging state.

As used herein, the terms "separator" and "membrane" will refer to an ionically conductive and electrically insulating material disposed between the positive and negative electrodes of an electrochemical cell. The separator can be a porous membrane in some embodiments and/or an ionomer membrane in other various embodiments. In some embodiments, the separator can be formed from an ionically conductive polymer.

Polymer membranes can be anion- or cation-conducting electrolytes. Where described as an "ionomer," the term refers to polymer membranes containing both electrically neutral repeating units and ionized repeating units, where the ionized repeating units are pendant and covalently bonded to the polymer backbone. In general, the fraction of ionized units can range from about 1 mole percent to about 90 mole percent. For example, in some embodiments, the content of ionized units is less than about 15 mole percent; and in other embodiments, the ionic content is higher, such as greater than about 80 mole percent. In still other embodiments, the ionic content is defined by an intermediate range, for example, in a range of about 15 to about 80 mole percent. Ionized repeating units in an ionomer can include anionic functional groups such as sulfonate, carboxylate, and the like. These functional groups can be charge balanced by, mono-, di-, or higher-valent cations, such as alkali or alkaline earth metals. Ionomers can also include polymer compositions containing attached or embedded quaternary ammonium, sulfonium, phosphazenium, and guanidinium residues or salts. Suitable examples will be familiar to one having ordinary skill in the art.

In some embodiments, polymers useful as a separator can include highly fluorinated or perfluorinated polymer backbones. Certain polymers useful in the present disclosure can include copolymers of tetrafluoroethylene and one or more fluorinated, acid-functional co-monomers, which are commercially available as NAFION™ perfluorinated polymer electrolytes from DuPont. Other useful perfluorinated polymers can include copolymers of tetrafluoroethylene and $FSO_2$—$CF_2CF_2CF_2CF_2$—O—CF=$CF_2$, FLEMION™ and SELEMION™.

Additionally, substantially non-fluorinated membranes that are modified with sulfonic acid groups (or cation exchanged sulfonate groups) can also be used. Such membranes can include those with substantially aromatic backbones such as, for example, polystyrene, polyphenylene, biphenyl sulfone (BPSH), or thermoplastics such as polyetherketones and polyethersulfones.

Battery-separator style porous membranes, can also be used as the separator. Because they contain no inherent ionic conduction capabilities, such membranes are typically impregnated with additives in order to function. These membranes typically contain a mixture of a polymer, and inorganic filler, and open porosity. Suitable polymers can include, for example, high density polyethylene, polypropylene, polyvinylidene difluoride (PVDF), or polytetrafluoroethylene (PTFE). Suitable inorganic fillers can include silicon carbide matrix material, titanium dioxide, silicon dioxide, zinc phosphide, and ceria.

Separators can also be formed from polyesters, polyetherketones, poly(vinyl chloride), vinyl polymers, and substituted vinyl polymers. These can be used alone or in combination with any previously described polymer.

Porous separators are non-conductive membranes which allow charge transfer between two electrodes via open channels filled with electrolyte. The permeability increases the probability of chemicals (e.g., active materials) passing through the separator from one electrode to another and causing cross-contamination and/or reduction in cell energy efficiency. The degree of this cross-contamination can depends on, among other features, the size (the effective diameter and channel length), and character (hydrophobicity/hydrophilicity) of the pores, the nature of the electrolyte, and the degree of wetting between the pores and the electrolyte.

The pore size distribution of a porous separator is generally sufficient to substantially prevent the crossover of active materials between the two electrolyte solutions. Suitable porous membranes can have an average pore size distribution of between about 0.001 nm and 20 micrometers, more typically between about 0.001 nm and 100 nm. The size distribution of the pores in the porous membrane can be substantial. In other words, a porous membrane can contain a first plurality of pores with a very small diameter (approximately less than 1 nm) and a second plurality of pores with a very large diameter (approximately greater than 10 micrometers). The larger pore sizes can lead to a higher amount of active material crossover. The ability for a porous membrane to substantially prevent the crossover of active materials can depend on the relative difference in size between the average pore size and the active material. For example, when the active material is a metal center in a coordination compound, the average diameter of the coordination compound can be about 50% greater than the average pore size of the porous membrane. On the other hand, if a porous membrane has substantially uniform pore sizes, the average diameter of the coordination compound can be about 20% larger than the average pore size of the porous membrane. Likewise, the average diameter of a coordination compound is increased when it is further coordinated with at least one water molecule. The diameter of a coordination compound of at least one water molecule is generally considered to be the hydrodynamic diameter. In such embodiments, the hydrodynamic diameter is generally at least about 35% greater than the average pore size. When the average pore size is substantially uniform, the hydrodynamic radius can be about 10% greater than the average pore size.

In some embodiments, the separator can also include reinforcement materials for greater stability. Suitable reinforcement materials can include polytetrafluoroethylene, nylon, cotton, polyesters, crystalline silica, crystalline titania, amorphous silica, amorphous titania, rubber, asbestos, wood or any combination thereof.

Separators within the flow batteries of the present disclosure can have a membrane thickness of less than about 500 micrometers, less than about 300 micrometers, less than about 250 micrometers, less than about 200 micrometers, less than about 100 micrometers, less than about 75 micrometers, less than about 50 micrometers, less than about 30 micrometers, less than about 25 micrometers, less than about 20 micrometers, less than about 15 micrometers, or less than about 10 micrometers. Suitable separators can include those in which the flow battery is capable of operating with a current efficiency of greater than about 85% with a current density of 100 mA/cm² when the separator has a thickness of 100 micrometers. In further embodiments, the flow battery is capable of operating at a current efficiency of greater than 99.5% when the separator has a thickness of less than about 50 micrometers, a current efficiency of greater than 99% when the separator has a thickness of less than about 25 micrometers, and a current efficiency of greater than 98% when the separator has a thickness of less than about 10 micrometers. Accordingly, suitable separators include those in which the flow battery is capable of operating at a voltage efficiency of greater than 60% with a current density of 100 mA/cm². In further embodiments, suitable separators can include those in which the flow battery is capable of operating at a voltage efficiency of greater than 70%, greater than 80% or even greater than 90%.

The diffusion rate of the first and second active materials through the separator can be less than about $1 \times 10^{-5}$ mol cm$^{-2}$ day$^{-1}$, less than about $1 \times 10^{-6}$ mol cm$^{-2}$ day$^{-1}$, less than about $1 \times 10^{-8}$ mol cm$^{-2}$ day$^{-1}$, less than about $1 \times 10^{-9}$ mol cm$^{-2}$ day$^{-1}$, less than about $1 \times 10^{-11}$ mol cm$^{-2}$ day$^{-1}$, less than about $1 \times 10^{-13}$ mol cm$^{-2}$ day$^{-1}$, or less than about $1 \times 10^{-15}$ mol cm$^{-2}$ day$^{-1}$.

The flow batteries can also include an external electrical circuit in electrical communication with the first and second electrodes. The circuit can charge and discharge the flow battery during operation. Reference to the sign of the net ionic charge of the first, second, or both active materials relates to the sign of the net ionic charge in both oxidized and reduced forms of the redox active materials under the conditions of the operating flow battery. Further exemplary embodiments of a flow battery provide that (a) the first active material has an associated net positive or negative charge and is capable of providing an oxidized or reduced form over an electric potential in a range the negative operating potential of the system, such that the resulting oxidized or reduced form of the first active material has the same charge sign (positive or negative) as the first active material and the ionomer membrane also has a net ionic charge of the same sign and (b) the second active material has an associated net positive or negative charge and is capable of providing an oxidized or reduced form over an electric potential in a range of the positive operating potential of the system, such that the resulting oxidized or reduced form of the second active material has the same charge sign (positive or negative sign) as the second active material and the ionomer membrane also has a net ionic charge of the same sign; or both (a) and (b). The matching charges of the first and/or second active materials and the ionomer membrane can provide a high selectivity. More specifically, charge matching can provide less than about 3%, less than about 2%, less than about 1%, less than about 0.5%, less than about 0.2%, or less than about 0.1% of the molar flux of ions passing through the ionomer membrane as being attributable to the first or second active material. The term "molar flux of ions" will refer to the amount of ions passing through the ionomer membrane, balancing the charge associated with the flow of external electricity/electrons. That is, the flow battery is capable of operating or operates with the substantial exclusion of the active materials by the ionomer membrane.

In some cases, a user may desire to provide higher charge or discharge voltages than available from a single battery cell. In such cases, several battery cells can be connected in series such that the voltage of each cell is additive. This forms a bipolar stack. An electrically conductive, but non-porous material (e.g., a bipolar plate) can be employed to connect adjacent battery cells in a bipolar stack, which allows for electron transport but prevents fluid or gas transport between adjacent cells. The positive electrode compartments and negative electrode compartments of individual cells can be fluidically connected via common positive and negative fluid manifolds in the stack. In this way, individual cells can be stacked in series to yield a voltage appropriate for DC applications or conversion to AC applications.

In additional embodiments, the cells, cell stacks, or batteries can be incorporated into larger energy storage systems, suitably including piping and controls useful for operation of these large units. Piping, control, and other equipment suitable for such systems are known in the art, and can include, for example, piping and pumps in fluid communication with the respective chambers for moving electrolyte solutions into and out of the respective chambers and storage tanks for holding charged and discharged electrolytes. The cells, cell stacks, and batteries of this disclosure can also include an operation management system. The operation management system can be any suitable controller device, such as a computer or microprocessor, and can contain logic circuitry that sets operation of any of the various valves, pumps, circulation loops, and the like.

In more specific embodiments, a flow battery system can include a flow battery (including a cell or cell stack); storage tanks and piping for containing and transporting the electrolyte solutions; control hardware and software (which may include safety systems); and a power conditioning unit. The flow battery cell stack accomplishes the conversion of charging and discharging cycles and determines the peak power. The storage tanks contain the positive and negative active materials, and the tank volume determines the quantity of energy stored in the system. The control software, hardware, and optional safety systems suitably include sensors, mitigation equipment and other electronic/hardware controls and safeguards to ensure safe, autonomous, and efficient operation of the flow battery system. A power conditioning unit can be used at the front end of the energy storage system to convert incoming and outgoing power to a voltage and current that is optimal for the energy storage system or the application. For the example of an energy storage system connected to an electrical grid, in a charging cycle the power conditioning unit can convert incoming AC electricity into DC electricity at an appropriate voltage and current for the cell stack. In a discharging cycle, the stack produces DC electrical power and the power conditioning unit converts it to AC electrical power at the appropriate voltage and frequency for grid applications.

Where not otherwise defined hereinabove or understood by one having ordinary skill in the art, the definitions in the following paragraphs will be applicable to the present disclosure.

As used herein, the term "energy density" will refer to the amount of energy that can be stored, per unit volume, in the active materials. Energy density refers to the theoretical energy density of energy storage and can be calculated by Equation 4

$$\text{Energy density}=(26.8\ A\text{-}h/\text{mol}) \times \text{OCV} \times [e^-] \quad \text{(Equation 4)}$$

where OCV is the open circuit potential at 50% state of charge, (26.8 A-h/mol) is Faraday's constant, and $[e^-]$ is the concentration of electrons stored in the active material at 99% state of charge. In the case that the active materials largely are an atomic or molecular species for both the positive and negative electrolyte, $[e^-]$ can be calculated by Equation 5 as $$[e^-]=[\text{active materials}] \times N/2 \quad \text{(Equation 5)}$$

where [active materials] is the molar concentration of the active material in either the negative or positive electrolyte, whichever is lower, and N is the number of electrons transferred per molecule of active material. The related term "charge density" will refer to the total amount of charge that each electrolyte contains. For a given electrolyte, the charge density can be calculated by Equation 6

$$\text{Charge density}=(26.8\ A\text{-}h/\text{mol}) \times [\text{active material}] \times N \quad \text{(Equation 6)}$$

where [active material] and N are as defined above.

As used herein, the term "current density" will refer to the total current passed in an electrochemical cell divided by the geometric area of the electrodes of the cell and is commonly reported in units of mA/cm².

As used herein, the term "current efficiency" ($I_{eff}$) can be described as the ratio of the total charge produced upon discharge of a cell to the total charge passed during charging. The current efficiency can be a function of the state of charge of the flow battery. In some non-limiting embodiments, the current efficiency can be evaluated over a state of charge range of about 35% to about 60%.

As used herein, the term "voltage efficiency" can be described as the ratio of the observed electrode potential, at a given current density, to the half-cell potential for that electrode (×100%). Voltage efficiencies can be described for a battery charging step, a discharging step, or a "round trip voltage efficiency." The round trip voltage efficiency ($V_{eff,rt}$) at a given current density can be calculated from the cell voltage at discharge ($V_{discharge}$) and the voltage at charge ($V_{charge}$) using equation 7:

$$V_{EFF,RT} = V_{discharge}/V_{charge} \times 100\%$$ (Equation 7)

As used herein, the terms "negative electrode" and "positive electrode" are electrodes defined with respect to one another, such that the negative electrode operates or is designed or intended to operate at a potential more negative than the positive electrode (and vice versa), independent of the actual potentials at which they operate, in both charging and discharging cycles. The negative electrode may or may not actually operate or be designed or intended to operate at a negative potential relative to a reversible hydrogen electrode. The negative electrode is associated with a first electrolyte solution and the positive electrode is associated with a second electrolyte solution, as described herein. The electrolyte solutions associated with the negative and positive electrodes may be described as negolytes and posolytes, respectively.

EXAMPLES

Figure 3:
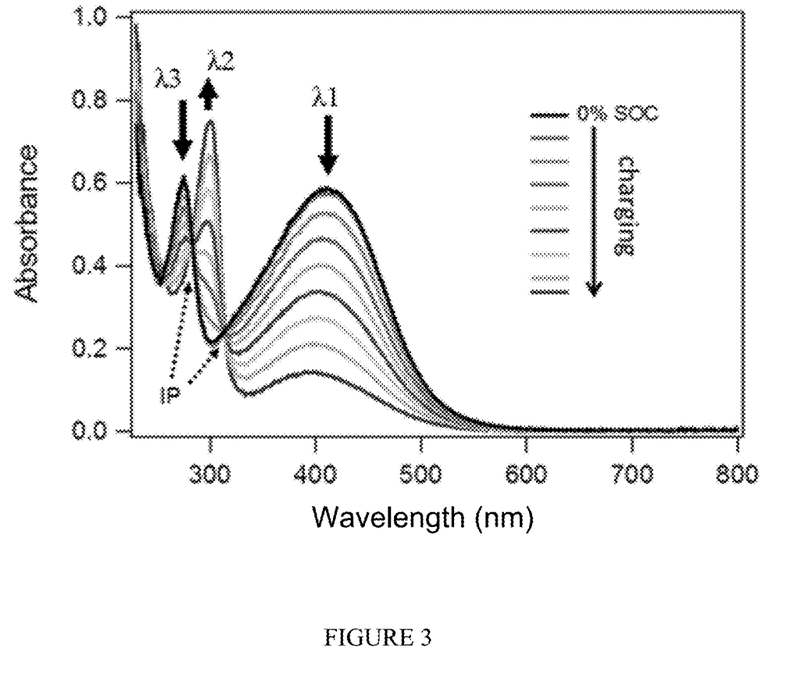
FIG. 3 shows an illustrative UV-VIS spectrum of an electrolyte solution containing $Ti^{3+/4+}(catecholate)_2(pyrogallate)$ as measured by ATR spectroscopy at various states of charge.

FIG. 3 shows an illustrative UV-VIS spectrum of an electrolyte solution containing $Ti^{3+/4+}$(catecholate)$_2$(pyrogallate) as measured by ATR spectroscopy at various states of charge. This coordination compound has a molar absorptivity constant of about 10,800 $M^{-1}cm^{-1}$ for the main absorption band at 380 nm, as determined by transmission UV-VIS spectroscopy. Under ATR conditions, this absorption band shifted to approximately 410 nm. The spectra were acquired by immersing an ATR probe with a sapphire tip in the electrolyte solution with the coordination compound initially in its fully oxidized state. The ATR probe was connected to a commercial UV-VIS spectrophotometer using fiber optics. The oxidized form of the coordination compound was then gradually converted into the reduced form, and UV-VIS spectra were acquired after each stage of the reduction. Upon reduction, the initial UV-VIS spectrum changed dramatically, namely producing decreased intensities at $\lambda_1$ and $\lambda_3$ and ingrowth of a new absorbance at $\lambda_2$. The spectra displayed isosbestic points at the locations marked as IP.

Although the disclosure has been described with reference to the disclosed embodiments, those skilled in the art will readily appreciate that these are only illustrative of the disclosure. It should be understood that various modifications can be made without departing from the spirit of the disclosure. The disclosure can be modified to incorporate any number of variations, alterations, substitutions or equivalent arrangements not heretofore described, but which are commensurate with the spirit and scope of the disclosure. Additionally, while various embodiments of the disclosure have been described, it is to be understood that aspects of the disclosure may include only some of the described embodiments. Accordingly, the disclosure is not to be seen as limited by the foregoing description.

What is claimed is the following:

1. A method comprising:
    providing an electrochemical system containing a first electrolyte solution in contact with a first electrode, the first electrolyte solution comprising a first coordination compound having an oxidized form and a reduced form;
    interacting electromagnetic radiation with the first electrolyte solution at a location within the electrochemical system, the electromagnetic radiation being delivered through an optical material configured to exhibit attenuated total reflectance at an interface between the optical material and the first electrolyte solution;
    wherein the optical material has a higher index of refraction than does the first electrolyte solution;
    receiving at a detector electromagnetic radiation that has interacted with the first electrolyte solution via one or more attenuated total reflections within the optical material; and
    measuring an absorbance of at least one of the oxidized form or the reduced form of the first coordination compound with the electromagnetic radiation that is received at the detector;
    wherein the electrochemical system comprises a flow battery.

2. The method of claim 1, further comprising:
    determining a state of charge of the first electrolyte solution in the electrochemical system.

3. The method of claim 2, further comprising:
    adjusting the first electrolyte solution based upon the state of charge.

4. The method of claim 3, wherein adjusting the first electrolyte solution comprises at least one of reconditioning or rebalancing the first electrolyte solution, diluting the first electrolyte solution, adding a further amount of the first coordination compound to the first electrolyte solution, increasing a current passing through the first electrolyte solution, decreasing a current passing through the first electrolyte solution, or any combination thereof.

5. The method of claim 2, further comprising:
    determining a concentration of at least one of the oxidized form or the reduced form of the first coordination compound based upon the absorbance measured at the detector.

6. The method of claim 1, wherein the electromagnetic radiation is interacted with the first electrolyte solution external to a cell defining the flow battery.

7. The method of claim 1, wherein the electromagnetic radiation is interacted with the first electrolyte solution in proximity to the first electrode.

8. The method of claim 1, wherein the optical material is selected from the group consisting of sapphire, germanium, fused silica, quartz, cubic zirconia, zinc selenide, diamond, and any combination thereof.

9. The method of claim 1, wherein the first coordination compound has a molar absorptivity constant of at least about 100 $M^{-1}cm^{-1}$.

10. The method of claim 9, wherein a product of concentration and molar absorptivity constant of the first coordination compound in the first electrolyte solution is at least about 100 cm$^{-1}$.

11. The method of claim 1, wherein the optical material is configured to provide between 1 and about 6 attenuated total reflectances at the interface with the first electrolyte solution.

12. The method of claim 1, wherein the electromagnetic radiation comprises one or more wavelengths ranging between about 180 nm and about 800 nm.

13. The method of claim 1, wherein the absorbance is measured at least at an isosbestic point exhibited by the oxidized form and the reduced form of the first coordination compound.

14. The method of claim 1, wherein a depth of penetration of the electromagnetic radiation into the first electrolyte solution ranges between about 0.05 microns and about 2 microns.

15. A method comprising:
providing an electrochemical system containing a first electrolyte solution in contact with a first electrode, the first electrolyte solution comprising a first coordination compound having an oxidized form and a reduced form;
interacting electromagnetic radiation with the first electrolyte solution at a location within the electrochemical system, the electromagnetic radiation being delivered through an optical material configured to exhibit attenuated total reflectance at an interface between the optical material and the first electrolyte solution;
wherein the optical material has a higher index of refraction than does the first electrolyte solution;
receiving at a detector electromagnetic radiation that has interacted with the first electrolyte solution via one or more attenuated total reflections within the optical material; and
measuring an absorbance of at least one of the oxidized form or the reduced form of the first coordination compound with the electromagnetic radiation that is received at the detector;
wherein the electromagnetic radiation is absorbed by only one of the oxidized form or the reduced form of the first coordination compound.

16. The method of claim 1, wherein the electromagnetic radiation is absorbed by both the oxidized form and the reduced form of the first coordination compound.

17. An electrochemical system comprising:
a first electrolyte solution in contact with a first electrode, the first electrolyte solution comprising a first coordination compound having an oxidized form and a reduced form;
a source of electromagnetic radiation;
an optical material establishing optical communication between the source of electromagnetic radiation and the first electrolyte solution;
wherein the optical material is configured to exhibit attenuated total reflectance at an interface between the optical material and the first electrolyte solution, the optical material having a higher index of refraction than does the first electrolyte solution; and
a detector configured to receive electromagnetic radiation from the optical material that has interacted with the first electrolyte solution via one or more attenuated total reflections at the interface between the optical material and the first electrolyte solution;
wherein the electrochemical system comprises a flow battery.

18. The electrochemical system of claim 17, wherein the optical material establishes optical communication with the first electrolyte solution outside a cell defining the flow battery.

19. The electrochemical system of claim 17, wherein the optical material establishes optical communication with the first electrolyte solution in proximity to the first electrode.

20. The electrochemical system of claim 17, wherein the optical material is selected from the group consisting of sapphire, germanium, fused silica, quartz, cubic zirconia, zinc selenide, diamond, and any combination thereof.

* * * * *